United States Patent
Dixon

(10) Patent No.: US 7,833,522 B2
(45) Date of Patent: Nov. 16, 2010

(54) APPARATUS AND METHOD TO TREAT A WOUND AREA

(76) Inventor: David M. Dixon, 826 N. Venice Ave., Tucson, AZ (US) 85711

( * ) Notice: Subject to any disclaimer, the term of this patent is extended or adjusted under 35 U.S.C. 154(b) by 455 days.

(21) Appl. No.: 11/462,965

(22) Filed: Aug. 7, 2006

(65) Prior Publication Data
US 2007/0031385 A1 Feb. 8, 2007

Related U.S. Application Data

(60) Provisional application No. 60/705,906, filed on Aug. 5, 2005.

(51) Int. Cl.
*A01N 63/00* (2006.01)
*A61K 35/12* (2006.01)
*A61K 35/36* (2006.01)
*A61K 38/00* (2006.01)

(52) U.S. Cl. .................. 424/93.7; 424/572; 424/574; 514/2; 514/21

(58) Field of Classification Search .............. 424/93.7
See application file for complete search history.

(56) References Cited

U.S. PATENT DOCUMENTS

| 1,806,784 A | | 5/1931 | Breuer |
| 5,688,236 A | * | 11/1997 | Gragg .................. 604/23 |
| 5,720,981 A | | 2/1998 | Eisinger |
| 5,980,888 A | * | 11/1999 | Dimoudis et al. ........ 424/93.7 |
| 6,048,728 A | * | 4/2000 | Inlow et al. ............. 435/404 |
| 6,461,361 B1 | * | 10/2002 | Epstein ................. 606/82 |
| 6,479,052 B1 | | 11/2002 | Marshall et al. |

FOREIGN PATENT DOCUMENTS

WO    WO 2005012508 A1 *   2/2005

* cited by examiner

*Primary Examiner*—Ruth A Davis
*Assistant Examiner*—Sheridan R Macauley
(74) *Attorney, Agent, or Firm*—Dale F. Regelman; Quarles & Brady LLP

(57) ABSTRACT

A method is disclosed to treat a patient having a wound area, such as a burn injury. The method provides a plurality of epidermal/dermal cells, and applies that plurality of epidermal/dermal cells to the wound area.

14 Claims, 3 Drawing Sheets

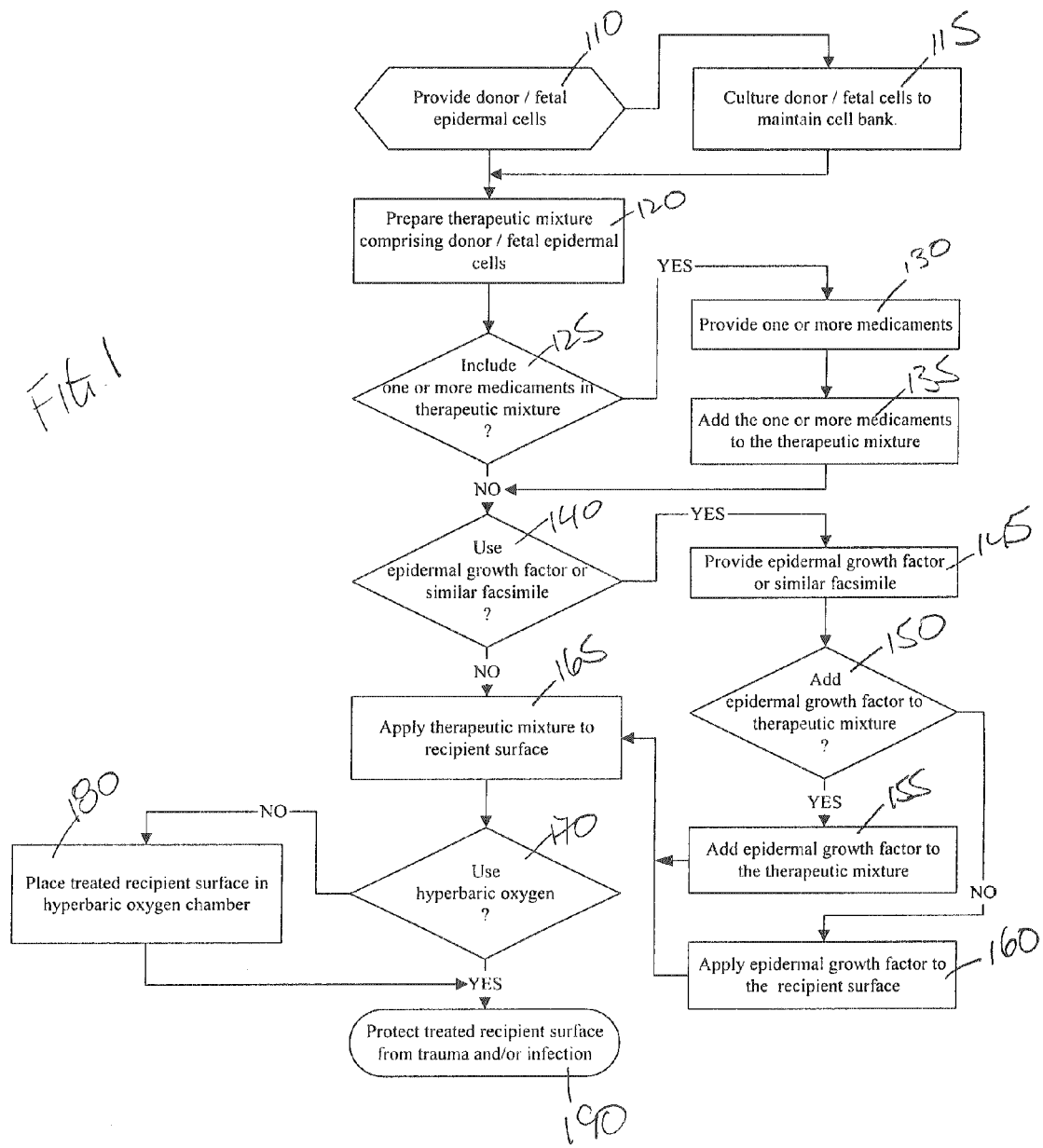

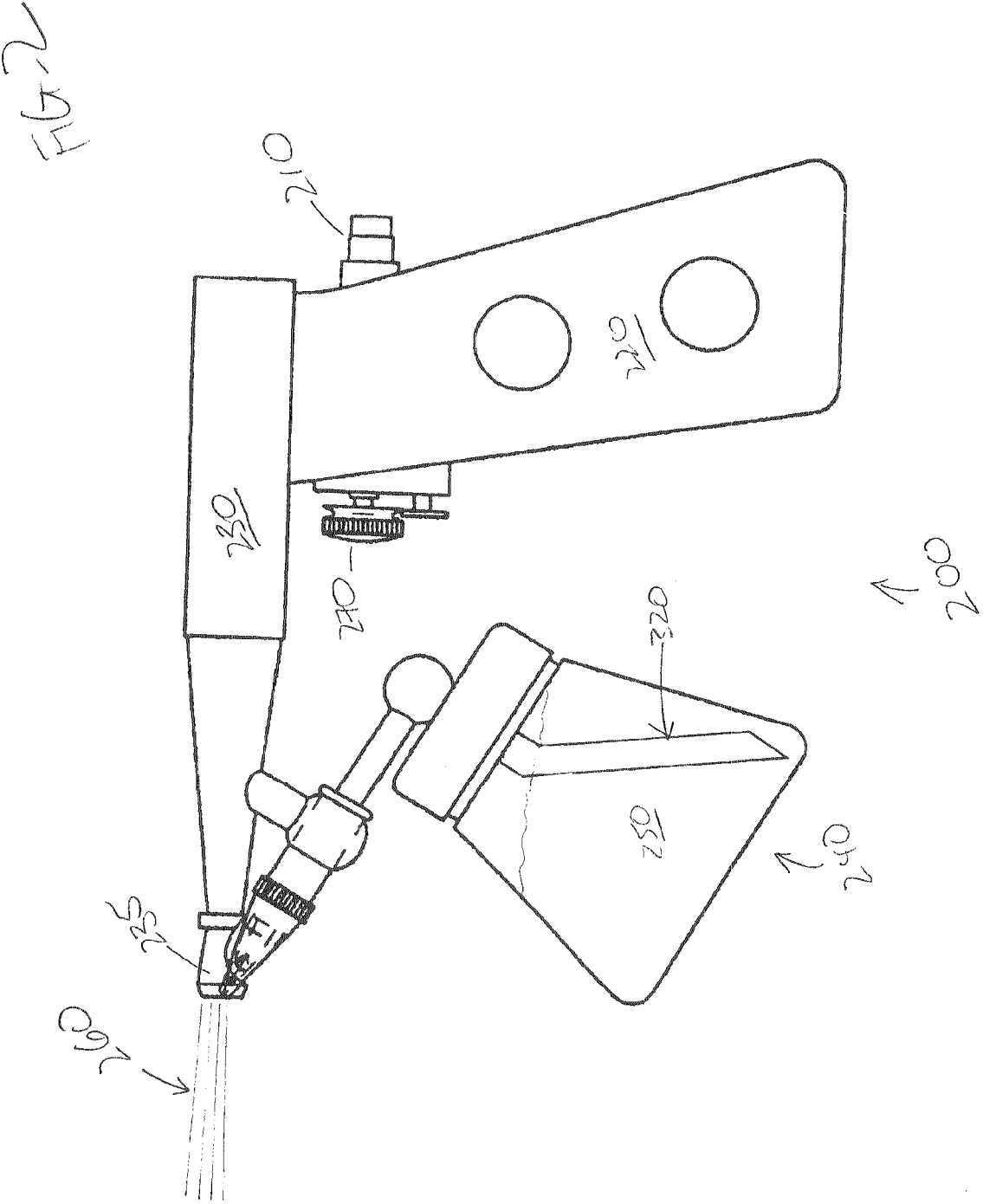

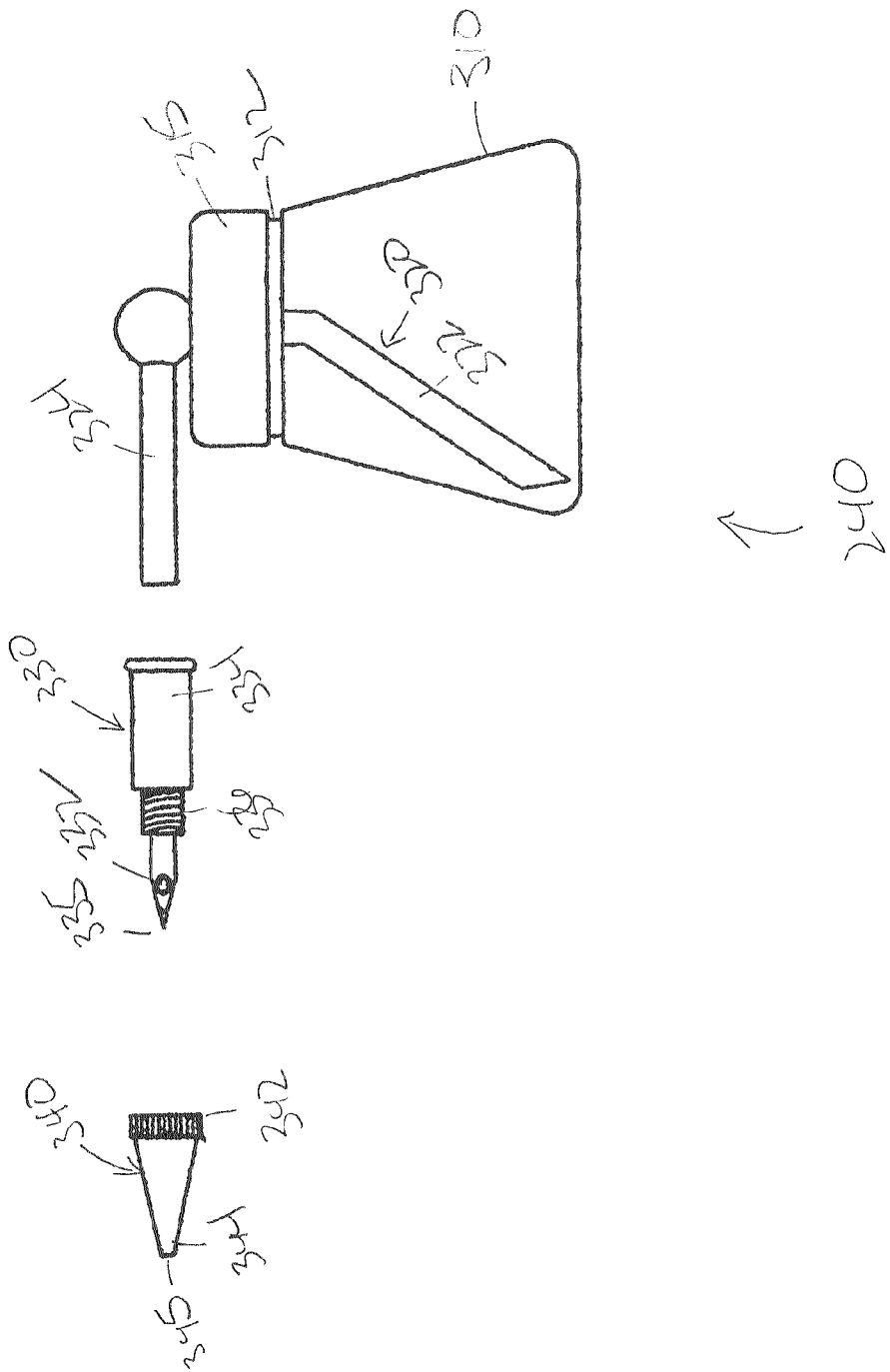

APPARATUS AND METHOD TO TREAT A WOUND AREA

CROSS-REFERENCE TO RELATED APPLICATIONS

This Application claims priority from a U.S. Provisional Application having Ser. No. 60/705,906, filed Aug. 5, 2005.

FIELD OF THE INVENTION

The invention is directed to an apparatus and method to treat a wound area. In certain embodiments, the invention is directed to an apparatus and method to treat a burn injury.

BACKGROUND OF THE INVENTION

While it is ideal to prevent burn injuries from ever happening, unexpected circumstances will always exist. Effective burn treatments help to minimize damage and complications while promoting healing and recovery. All burn injuries are potentially dangerous; that's why healthcare professionals check for immediate injury as well as monitor for delayed complications. If a burn injury is severe, it often requires emergency treatment to prevent shock and infection.

Debridement and excision are both methods of cleansing or preparing a burn wound for proper assessment, classification and treatment. Healthcare professionals perform these procedures for two important reasons—to remove damaged tissue and promote healing.

Debridement removes dead tissue and blisters to expose the true depth and severity of a wound. In some burn injuries, dead tissue naturally falls off as part of the healing process. However, in most cases, active debridement is used to remove damaged skin. Debridement is often an extremely painful procedure. Such removal of damaged tissues is necessary, however, for protection from bacteria and other complications. There are four primary methods of debridement, including: (1) Autolytic-allowing the body to naturally rid itself of dead tissue, (2) Enzymatic-using chemical enzymes to free dead tissue, (3) Mechanical-removing dead tissue through the use of hydrotherapy (water), and (4) Surgical-using sharp instruments or lasers for debridement.

Excision is usually an option for burn wounds determined to be deep second degree or full thickness third degree. This process surgically removes dead tissue in order to prepare a wound for a skin graft or other skin replacement procedure. Thin layers of burned skin are removed until living tissue is exposed. The wound is then cleansed and prepared for grafting.

Treatment of severe burns often requires skin grafting. Prior art methods involve taking skin, both the epidermis and dermis, from unburned sites on the body, i.e. donor sites, and grafting that skin onto the burn wound. The grafted skin attaches to the underlying tissue and effectively closes the wound.

A graft "takes" or is successful when new blood vessels and tissue form in the injured area. Sometimes, skin grafts do not take because of complications such as infection (the most common cause of graft failure) or shearing (pressure causing a graft to detach from the skin). While grafting is a proven and effective treatment, it is important to understand that all prior art skin grafts leave some scarring at both the donor and recipient sites.

By using a patient's own skin to cover a burn wound, the risk of tissue rejection is eliminated. However, skin grafts are often a challenge for patients with severe burns across large portions of their body. In these instances there may not be sufficient donor site skin to immediately cover all of the individual's wounds.

Skin flaps are a complex type of skin graft that attach donor skin and underlying tissue by surgically connecting blood supply from the wound to the transferred skin. Skin flaps and other skin replacement methods are sometimes used in situations where standard skin grafts are not possible or where alternative methods are preferred.

Split-thickness skin grafts (STSGs) are grafts that include the epidermal and part of the dermal skin layers. Grafts up to four inches wide and 10-12 inches long can be removed from flat body surfaces such as the abdomen, thigh or back. These grafts are sewn or stapled into place and covered with compression dressings (tightly wrapped elastic bandages) to provide firm contact. Occasionally, graft sites are left open to air.

Split-thickness grafts are generally not used for weight-bearing parts of the body or for areas subject to friction such as hands or feet. Generally, STSGs are applied as intact sheets or, if there is too little donor skin available, meshed and expanded to maximize graft coverage area. Meshing involves cutting tiny holes in the donor skin so it can be stretched to cover more surface area. The advantages of STSGs include less tissue use, an improved chance of graft survival and minimized donor site damage. However, one disadvantage is that STSGs tend to contract more than full-thickness skin grafts.

Full-thickness skin grafts (FTSGS) consist of both the epidermal and complete dermal skin layers. This type of graft is used instead of a split-thickness skin graft when cosmetic outcome is essential and a skin flap is not available. The thicker the FTSG, the less the potential for contraction. Other advantages include increased resistance to trauma over thin grafts and less distortion functionally and cosmetically.

| Comparison of Split-Thickness and Full-Thickness Skin Grafts | | |
|---|---|---|
| Feature | STSG | FTSG |
| Composition | Epidermis + part of the dermis | Epidermis + dermis + various amounts of fat |
| Graft Survival | Greater chance of graft survival | Less chance of graft survival |
| Resistance to Trauma | Less resistant | More resistant |
| Cosmetic Appearance | Poor cosmetic appearance owing to poor color and texture match. Does not prevent contraction. | Superior cosmetic appearance. It is thicker, preventing wound contraction or distortion. |
| When Used | Temporarily or permanently after excision of a burn injury when there is adequate blood supply. | When aesthetic outcome is essential (e.g., facial defects). |
| Donor Site Tissue | Thigh, buttock, abdomen, inner or outer arm, inner forearm. | Nearby site, with similar color or texture to skin surrounding the defect. |
| Disadvantages | Poor cosmetic appearance, greater chance of distortion or contraction. | Greater risk of graft failure. Donor site wound requires prolonged healing time and has a greater risk of distortion and hypertrophic scar formation. |

Sometimes, the area requiring reconstruction lacks the blood supply needed to support a skin graft. The tissues used to reconstruct these wounds must carry their own blood supply. Skin flaps, an advanced form of skin grafting, is a complex procedure in which skin, along with underlying fat, blood vessels and sometimes muscle, is moved from a healthy part of the body to the injured site. In skin flaps located adjacent to the wound site, blood supply may remain attached at the donor site. In instances where the skin flap needs to be attached to a wound elsewhere on the body, surgeons will reattach blood vessels in the flap at the new site through microvascular surgery.

Cosmetically, skin flaps generally produce better results than typical skin grafts because they are often taken from the skin surrounding the injury. This provides the graft superior color and texture match.

When performing a skin graft, special care must be taken to prevent the creation of another difficult-to-heal wound or scar at the donor site. Thick split-thickness and full-thickness skin grafts result in deeper donor site wounds which require longer healing time and may result in contraction and hypertrophic scarring.

With deep split-thickness and full-thickness skin grafts, dermal tissue may be permanently lost at the donor site. The dermal layer cannot grow back by itself and most often results in scar formation. Healing time for most split-thickness skin grafts is approximately 10 to 20 days. Most full-thickness skin grafts require a longer 21 to 90 day period. As a result, medium-thickness split grafts are frequently used as a compromise to provide improved graft survival and durability with minimized donor site complications.

What is needed is an apparatus and method to form a nascent skin graft on a wound area by applying a plurality of individual epidermal cells to that wound area. Applicant's invention comprises such an apparatus and method to apply a plurality of individual epidermal cells to a wound area.

SUMMARY OF THE INVENTION

Applicant's invention comprises a method to treat a patient having a wound area, such as a burn injury. The method provides a plurality of epidermal cells, and applies that plurality of epidermal cells to the wound area.

BRIEF DESCRIPTION OF THE DRAWINGS

The invention will be better understood from a reading of the following detailed description taken in conjunction with the drawings in which like reference designators are used to designate like elements, and in which:

FIG. 1 is a flow chart summarizing the steps of Applicant's method;

FIG. 2 is a side view of Applicant's apparatus to apply a plurality of epidermal cells to a wound area; and FIG. 3 is a side view showing a portion of the apparatus of FIG. 2 in greater detail.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or mere embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In marked distinction to use of a prior art split-thickness skin graft ("STSG") or a prior art medium-thickness skin graft, or a prior art full-thickness skin graft ("FTSG"), Applicant's invention comprises an apparatus and a method to form a nascent skin graft to a recipient area. Applicant's method provides a plurality of individual epidermal cells, and applies that plurality of epidermal cells to a recipient area, i.e. the wound area. In certain embodiments, such a recipient area comprises a burn injury. In certain embodiments, such a recipient area comprises a burn injury that has been debrided.

Treatment of a burn injury using Applicant's nascent skin graft provides many of the advantages realized using an STSG in combination with many of the advantages realized in using a FTSG. For example, Applicant's nascent skin graft has a chance of survival comparable to an FTSG while providing a cosmetic appearance comparable to an STSG. In addition, Applicant's method spares the patient the large scars necessarily resulting from the harvesting the tissue from another part of the body.

Referring now to FIG. 1, in step 110 Applicant's method provides a plurality of individual fetal epidermal cells; a plurality of the patient's own donor individual epidermal cells taken from a small donor area; and/or combinations thereof. In certain embodiments, that fetal epidermis is between about 3 to about 4 months of age in utero. As those skilled in the art will appreciate, fetal epidermis at this age begins to differentiate to form the future sebaceous glands, hair follicles, and other constituents of adult epidermis. As those skilled in the art will further appreciate, such fetal tissue is theoretically antigenically neutral. Applicant has further discovered that such transplanted fetal epidermis, and/or the patient's own donor epidermal cells, may potentially form all of the constituents of adult skin, including without limitation hair follicles, after those cells "take".

In certain embodiments, Applicant's method includes step 115 wherein the fetal epidermal cells and/or the patient's own donor epidermal cells are cultured in a medium to keep a "bank" of cells that are continually grown. In certain embodiments, that medium is selected from the group consisting of thioglycolate, tryptic soybroth, chocolate agar, combinations thereof, and the like.

In step 120, Applicant's method forms a therapeutic mixture comprising the donor and/or fetal epidermal cells. In certain embodiments, the therapeutic mixture of step 120 comprises a carrier in combination with the donor and/or fetal epidermal cells of step 110. In certain embodiments, that carrier comprises isotonic saline; recipients blood serum; or any carrier that will not compromise the donor cells. In certain embodiments, that carrier comprises hypotonic saline solution. In certain embodiments, the donor and/or fetal epidermal cells comprise between about 3 weight percent to about 76 weight percent of Applicant's therapeutic mixture. In certain embodiments, the donor and/or fetal epidermal cells comprise about 19 weight percent of Applicant's therapeutic mixture.

In step 125, Applicant's method determines whether to include one or more medicaments to Applicant's therapeutic mixture. If one or more medicaments are not to be applied in combination with the donor and/or fetal epidermal cells, then Applicant's method transitions from step 125 to step 140.

Alternatively, if one or more medicaments are to be applied in combination with the selected epidermal cells, then the method transitions from step 125 to step 130 wherein Applicant's method provides those one or more medicaments. In certain embodiments, such one or more medicaments comprise antibiotics, steroids, anti-fungals, combinations thereof, and the like. In step 135, the one or more medicaments are added to the therapeutic mixture.

Applicant's method transitions from step 135 to step 140 wherein Applicant's method determines whether to utilize an epidermal growth factor, or a similar facsimile. As those skilled in the art will appreciate, an epidermal growth factor comprises a cell messenger protein that has effects including stimulation of epidermal development. If an epidermal growth factor is not being utilized, then the method transitions from step 140 to step 165.

Alternatively, if an epidermal growth factor is being utilized, then the method transitions from step 140 to step 145 wherein the method provides that epidermal growth factor, or similar facsimile. Applicant's method transitions from step 145 to step 150 wherein the method determines whether to add the epidermal growth factor of step 145 to Applicant's therapeutic mixture.

If Applicant's method adds the epidermal growth factor to Applicant's therapeutic mixture, then the method transitions from step 150 to step 155 wherein the method adds the epidermal growth factor of step 145 to Applicant's therapeutic mixture. Applicant's method transitions from step 155 to step 165.

If Applicant's method does not add the epidermal growth factor to Applicant's therapeutic mixture, then the method transitions from step 150 to step 160 wherein the method applies the epidermal growth factor directly to the recipient surface. Applicant's method transitions from step 160 to step 165 wherein Applicant's therapeutic mixture is applied to the recipient area. In certain embodiments, step 165 includes using Applicant's apparatus described hereinbelow. In certain embodiments, step 165 comprises forming on the recipient surface a nascent skin graft comprising donor and/or fetal epidermal cells, wherein that nascent skin graft comprises a thickness of one to two or more cell layers.

Applicant's method transitions from step 165 to step 170 wherein the method determines whether to utilize hyperbaric oxygen to promote growth of a new basal layer of transplanted epidermis/dermis progenitor cells. If Applicant's method does not elect to utilize hyperbaric oxygen, then the method transitions from step 170 to step 190 wherein the nascent skin graft is protected from trauma and/or infection.

If Applicant's method elects in step 170 to utilize hyperbaric oxygen, then the method transitions from step 170 to step 180 wherein the debrided wound area newly-covered with the spray-applied donor and/or fetal epidermal cells is disposed in a hyperbaric oxygen chamber to augment attachment of the cells by keeping them viable in the oxygen rich environment until a collateral circulation is established. Applicant's method transitions from step 180 to step 190.

In certain embodiments, step 165 comprises applying a layer of fetal progenitor epidermal/dermal cells and/or donor (autologous) progenitor epidermal/dermal cells using Applicant's epidermal/dermal progenitor cell spray apparatus. Referring now to FIG. 2, Applicant's cell spray apparatus 200 comprises gas inlet 210, handle 220, barrel 230, reservoir assembly 240, and trigger mechanism 270. In the illustrated embodiment of FIG. 2, reservoir 240 is partially filled with Applicant's donor and/or fetal epidermal/dermal cell mixture 250. In certain embodiments, cell spray apparatus 200 is used one time only, and then discarded.

In certain embodiments, cell spray apparatus 200 can be sterilized using an Autoclave. In certain embodiments, apparatus is formed from stainless steel and can be sterilized using up to about 30 psi steam at a temperature of up to about 132° C. for up to about 15 minutes, or sterilized using dry heat at temperatures up to about 170° C. for up to about 60 minutes.

Referring now to FIG. 3, reservoir assembly 240 comprises container 310, cap 315, tubular member 320, needle valve assembly 330, and rotatable tubular assembly 340. Cap 315 can be releaseably affixed to container 310. In certain embodiments, top portion 312 of container 310 can be threadedly engaged with cap 315. First portion 322 of tubular member 320 extends through cap 315 into container 310. Second portion 324 of tubular member 320 extends outwardly from container 310. In certain embodiments, the orientation of first part 322 with respect to second part 324 is adjustable. For example comparing the illustrated embodiments of FIGS. 2 and 3, in FIG. 3 first part 322 has been rotated about 180 degrees from the illustrated embodiment of FIG. 2. If therapeutic mixture 250 is being sprayed upwardly, then the orientation of FIG. 2 is employed. If therapeutic mixture 250 is being sprayed upwardly, however, the orientation of FIG. 3 is employed.

Needle valve 330 is disposed on the distal end of portion 324 of tubular member 320. Proximal portion 334 of needle valve assembly 330 comprises a tubular member having an inner diameter of about 5-7 mm. Connecting portion 336 of assembly 330 interconnects proximal portion 334 and distal portion 335. In the illustrated embodiment of FIG. 3, connecting portion 336 comprises a threaded exterior surface. Needle valve assembly 330 is formed to comprise orifice 332 which extends through distal end 335 of assembly 330. In the illustrated embodiment of FIG. 3, distal end 335 tapers to a sharp point. In certain embodiments, orifice 332 comprises a diameter about 50 to about 100 times the diameter of the epidermal cells comprising therapeutic mixture 250.

If the diameter of orifice 332 is too small, then the fetal/donor cells passing through orifice 332 may be damaged. On the other hand, if the diameter of orifice 332 is too large, then unacceptably large "clumps" of fetal/donor cells may be sprayed.

For example, if the patient's donor cells have a diameter of about 20 microns, then orifice 332 has a diameter of between about 1 millimeter to about 2 millimeters. If on the other hand, fetal epidermal cells having an average diameter of 10 microns are used, then orifice 332 has a diameter of between about 0.5 millimeter to about 1 millimeter.

Tubular rotatable assembly 340 can be releaseably connected to needle valve assembly 330. In certain embodiments, proximal portion 342 of tubular rotatable assembly 340 comprises a first inner diameter which is threaded and which can be threadedly engaged with connecting portion 336 of assembly 330. Tubular rotatable assembly 340 tapers from proximal end 342 to distal end 344 which comprises a second diameter, wherein the second diameter is smaller than the first diameter. Distal end 344 is formed to include orifice 345. In certain embodiments, orifice 345 has a diameter between about 100 times and about 250 times the diameter of the fetal/donor cells comprising therapeutic mixture 250. Orifice 345 is dimensioned such that end portion 335 of assembly 330 can be inserted into orifice 345 such that end portion 335 extends into and closes orifice 345.

Rotating assembly 340 in a first direction causes assembly 340 to move outwardly from assembly 330 thereby increasing the distance between end portion 335 and orifice 345. Rotating assembly 340 is a second, i.e. opposite, direction causes assembly 340 to move inwardly toward assembly 330, and eventually causes end portion 335 to extend into and close orifice 345.

Referring now to FIGS. 2 and 3, when trigger mechanism 270 is depressed, pressurized gas is provided from an external gas source interconnected to gas inlet 210. As that pressurized gas flows past distal portion 235 of barrel 230 and past orifice 345, the resulting Venturi effect causes Applicant's therapeutic mixture 250 to flow outwardly from container 310, through orifice 345, and into that pressurized gas to form spray 260. Spray 260 is propelled outwardly from distal end 235 of barrel 230. Spray 260 is then directed onto a recipient surface to deposit a consistent layer of cells thereon.

Applicant has found that the diameter of aperture 345 should be at least 1.5 mm or greater. Conventional spray equipment utilizes an aperture of about 1 mm. Applicant has found that use of such an aperture comprising that small an aperture may result in damage to the sprayed fetal/donor cells. Applicant has further discovered that such damaged cells are no longer viable when they are deposited on the recipient surface, due to the destructive "shear" forces exerted on them if the aperture orifice is too small.

In addition, Applicant has discovered that the pressure of the one or more gases introduced at inlet 210 must be lower than about 125 psi. Use of one or more propellant gases having a pressure greater than about 125 psi may result in damage to the sprayed fetal/donor cells. Applicant has further discovered that such damaged cells are no longer viable when they come into contact with the recipient surface. In certain embodiments, cell spray apparatus 200 utilizes a propellant gas having a pressure of between about 10 to about 44 psi.

While the preferred embodiments of the present invention have been illustrated in detail, it should be apparent that modifications and adaptations to those embodiments may occur to one skilled in the art without departing from the scope of the present invention as set forth in the following claims.

I claim:

1. A method to treat a patient having a wound area, comprising the steps of:

providing a plurality of epidermal and/or dermal cells, wherein said epidermal and/or dermal cells comprise a cell diameter;

providing a spraying apparatus comprising a gas inlet, a barrel interconnected with said gas inlet, and reservoir assembly interconnected with said barrel;

wherein said reservoir assembly further comprises a container; a first tubular member comprising a proximal portion disposed within said container and a distal portion extending outwardly from said container; a needle valve interconnected with said distal end of said first tubular member, wherein said needle valve is formed to include a first orifice comprising a first diameter between about 50 to about 100 times said cell diameter; a second tubular member having a proximal portion and a distal portion, wherein said needle valve is disposed within said proximal portion of said second tubular member, and wherein said distal portion of said second tubular member is disposed within said barrel, and wherein said distal end of said second tubular member is formed to comprise a second orifice comprising a second diameter between about 100 to 250 times said cell diameter;

preparing a therapeutic mixture comprising said epidermal and/or dermal cells and a liquid carrier disposing said therapeutic mixture in said reservoir assembly;

interconnecting a source of pressurized gas to said gas inlet, wherein said pressurized gas comprises a pressure of between about 10 to about 44 psi at said gas inlet;

directing pressurized gas through said barrel;

mixing said therapeutic mixture and said pressurized gas in said barrel;

emitting from said barrel a spray comprising said pressurized gas and said therapeutic mixture; and directing said spray onto said wound area to deposit a layer of epidermal and/or dermal cells thereon.

2. The method of claim 1, wherein said providing a plurality of epidermal and/or dermal cells further comprises the steps of:

obtaining a plurality of donor epidermal and/or dermal cells from a donor area disposed on said patient's skin, wherein said donor area differs from said wound area;

culturing said plurality of donor epidermal and/or dermal cells in a medium, wherein said medium is selected from the group consisting of thioglycolate, tryptic soybroth, chocolate agar, and combinations thereof.

3. The method of claim 1, wherein said providing a plurality of epidermal and/or dermal cells further comprises providing a plurality of fetal epidermal and/or dermal cells.

4. The method of claim 1, wherein said wound area comprises a burn injury.

5. The method of claim 1, wherein said preparing a therapeutic mixture step comprises preparing a mixture of said epidermal and/or dermal cells in said carrier wherein said epidermal and/or dermal cells comprise between about 3 weight percent to about 76 weight percent of said therapeutic mixture.

6. The method of claim 5, wherein said preparing a therapeutic mixture step comprises preparing a mixture of said epidermal and/or dermal cells in said carrier wherein said epidermal and/or dermal cells comprise 19 weight percent of said therapeutic mixture.

7. The method of claim 1, further comprising the steps of:

providing one or more medicaments;

adding said one or more medicaments to said therapeutic mixture before applying said therapeutic mixture to said wound area.

8. The method of claim 1, further comprising the steps of:

providing epidermal growth factor;

applying said epidermal growth factor to said wound area.

9. The method of claim 8, wherein said applying said epidermal growth factor, step further comprises adding said epidermal growth factor to said therapeutic mixture before applying said therapeutic mixture to said wound area.

10. The method of claim 1, wherein:

said epidermal and/or dermal cells comprise donor cells having a diameter of about 20 microns;

said second diameter is about 5 millimeters.

11. The method of claim 10, wherein:

said epidermal and/or dermal cells comprise fetal epidermal cells comprising a diameter of about 10 microns;

said first diameter is about 0.5 millimeters.

12. The method of claim 1, further comprising the step of placing said wound area into a hyperbaric oxygen chamber after depositing a layer of epidermal cells thereon.

13. The method of claim 1, further comprising the step of protecting treated recipient surface from trauma and/or infection after depositing a layer of epidermal cells thereon in a sterile environment.

14. The method of claim 1, further comprising the step of protecting treated recipient surface from trauma and/or infection after depositing a layer of epidermal cells thereon in a non-sterile environment.

* * * * *